(12) United States Patent
West

(10) Patent No.: US 8,539,622 B2
(45) Date of Patent: Sep. 24, 2013

(54) OPERATING TABLE PATIENT POSITIONER AND METHOD

(76) Inventor: Tamra West, Rochester, NY (US)

( * ) Notice: Subject to any disclaimer, the term of this patent is extended or adjusted under 35 U.S.C. 154(b) by 462 days.

(21) Appl. No.: 12/953,749

(22) Filed: Nov. 24, 2010

(65) Prior Publication Data

US 2011/0219546 A1 Sep. 15, 2011

Related U.S. Application Data

(63) Continuation-in-part of application No. 12/722,610, filed on Mar. 12, 2010.

(60) Provisional application No. 61/215,169, filed on May 4, 2009.

(51) Int. Cl.
A47B 7/00 (2006.01)

(52) U.S. Cl.
USPC ............. 5/621; 5/623; 5/646; 5/647; 5/628

(58) Field of Classification Search
USPC ..... 5/621, 623, 646, 647, 628; 128/869–871, 128/876–878
See application file for complete search history.

(56) References Cited

U.S. PATENT DOCUMENTS

| | | | | |
|---|---|---|---|---|
| 455,778 A | * | 7/1891 | Tell | 296/20 |
| 721,587 A | * | 2/1903 | Lyons | 5/621 |
| 746,311 A | * | 12/1903 | Emigh | 5/607 |
| 2,033,779 A | * | 3/1936 | Monk | 5/627 |
| 2,191,097 A | * | 2/1940 | Morrison | 602/19 |
| 2,309,464 A | * | 1/1943 | Lucci et al. | 5/628 |
| 2,366,082 A | * | 12/1944 | Baker | 5/628 |
| 2,394,264 A | * | 2/1946 | Robinson | 5/628 |
| 2,475,003 A | * | 7/1949 | Black | 606/243 |
| 2,845,314 A | * | 7/1958 | Long | 5/621 |
| 3,046,982 A | * | 7/1962 | Davis | 128/875 |
| 3,063,447 A | * | 11/1962 | Kirsten | 128/876 |
| 3,152,802 A | * | 10/1964 | Heisler et al. | 482/144 |
| 3,158,875 A | * | 12/1964 | Fletcher | 5/628 |
| 3,204,256 A | * | 9/1965 | Stollenwerk | 5/628 |
| 3,700,229 A | * | 10/1972 | Kurokawa et al. | 5/601 |
| 3,721,434 A | * | 3/1973 | Spies | 5/655 |

(Continued)

Primary Examiner — Robert G Santos
Assistant Examiner — David E Sosnowski
(74) Attorney, Agent, or Firm — Tracy Jong Law Firm; Tracy P. Jong; Cheng Ning Jong

(57) ABSTRACT

A patient positioner for maintaining a patient's position during a medical procedure is provided. The patient positioner includes a generally rectangular body anchoring portion having a longitudinally disposed head and tail ends and two transversely disposed opposing side ends, placeable atop an operating table. There are a pair of spaced apart chest straps, a pair of spaced apart table straps, a pair of upper arm straps, and a pair of wrist straps. There is a generally rectangular substrate backing having a longitudinally disposed head and tail ends and two transversely disposed opposing side ends, substantially concentrically disposed on and fixedly attached to the body anchoring portion. In use, the body anchoring portion is positioned under the patient's torso with the substrate backing side ends wrapped over the arms while the chest straps are brought over the patient's shoulders and criss-crossed over the patient's chest and secured on an opposing side rail while the upper arm and wrist straps are brought from underneath the patient's torso and wrapped over the patient's arms. The table straps are placed through a break of the operating table and secured to a surface underneath the operating table to prevent the patient from sliding toward the head end of the operating table in the Trendelenburg position.

9 Claims, 10 Drawing Sheets

(56) References Cited

U.S. PATENT DOCUMENTS

| | | | | |
|---|---|---|---|---|
| 3,729,752 | A * | 5/1973 | Huggins | 5/93.1 |
| 3,732,863 | A * | 5/1973 | Harrington | 602/19 |
| 3,861,666 | A * | 1/1975 | Nishiyama et al. | 5/601 |
| 3,892,399 | A * | 7/1975 | Cabansag | 378/174 |
| 3,933,154 | A * | 1/1976 | Cabansag | 128/870 |
| 4,067,565 | A * | 1/1978 | Daniels | 5/601 |
| 4,205,669 | A * | 6/1980 | Hamann | 5/603 |
| 4,252,113 | A * | 2/1981 | Scire | 5/628 |
| 4,488,715 | A * | 12/1984 | Comeau | 5/647 |
| 4,506,664 | A * | 3/1985 | Brault | 5/628 |
| 4,522,381 | A * | 6/1985 | Ludwick | 5/621 |
| 4,566,445 | A * | 1/1986 | Jelsma et al. | 606/242 |
| 4,601,075 | A * | 7/1986 | Smith | 5/628 |
| 4,616,637 | A * | 10/1986 | Caspari et al. | 602/39 |
| 4,662,366 | A * | 5/1987 | Tari | 128/877 |
| 4,669,106 | A * | 5/1987 | Ammerman | 378/208 |
| 4,674,483 | A * | 6/1987 | Frederick | 602/40 |
| 4,729,138 | A * | 3/1988 | Heyman et al. | 5/658 |
| 4,766,892 | A * | 8/1988 | Kreitman | 5/623 |
| 4,779,858 | A * | 10/1988 | Saussereau | 5/601 |
| 5,014,374 | A * | 5/1991 | Williams | 5/628 |
| 5,014,724 | A * | 5/1991 | Miller | 128/870 |
| 5,121,743 | A * | 6/1992 | Bishop | 602/22 |
| 5,179,746 | A * | 1/1993 | Rogers | 5/625 |
| 5,211,186 | A * | 5/1993 | Shoemaker et al. | 5/628 |
| 5,228,457 | A * | 7/1993 | Kawamura | 5/607 |
| 5,263,214 | A * | 11/1993 | McLaughlin et al. | 5/628 |
| 5,342,290 | A * | 8/1994 | Schuellein | 602/36 |
| 5,515,869 | A * | 5/1996 | Powell et al. | 5/628 |
| 5,634,222 | A * | 6/1997 | Zwickey | 5/628 |
| 5,701,619 | A * | 12/1997 | Ullman | 5/625 |
| 5,718,671 | A * | 2/1998 | Bzoch | 602/20 |
| 5,729,850 | A * | 3/1998 | Eskeli | 5/621 |
| 5,785,057 | A * | 7/1998 | Fischer | 128/846 |
| 5,860,176 | A * | 1/1999 | Norberg | 5/628 |
| 6,154,902 | A * | 12/2000 | Russillio et al. | 5/623 |
| 6,568,010 | B1 * | 5/2003 | Ames | 5/646 |
| 6,622,324 | B2 | 9/2003 | VanSteenburg | |
| 6,691,351 | B1 * | 2/2004 | Wharton | 5/628 |
| 6,772,764 | B2 * | 8/2004 | Chapman | 128/870 |
| 6,860,272 | B2 * | 3/2005 | Carter et al. | 128/870 |
| 6,871,368 | B2 * | 3/2005 | Calkin | 5/628 |
| 6,898,811 | B2 * | 5/2005 | Zucker et al. | 5/626 |
| 6,966,087 | B2 * | 11/2005 | Robinette | 5/625 |
| 6,966,321 | B2 * | 11/2005 | Hess | 128/870 |
| 7,103,930 | B1 * | 9/2006 | Addesso-Dodd | 5/601 |
| 7,610,641 | B2 * | 11/2009 | Frost | 5/628 |
| 7,614,102 | B2 * | 11/2009 | Helt et al. | 5/625 |
| 7,752,722 | B2 * | 7/2010 | Calkin | 24/632 |
| 7,861,341 | B2 * | 1/2011 | Ayette et al. | 5/621 |
| 7,962,982 | B1 * | 6/2011 | Fellrath | 5/621 |
| 8,001,634 | B2 * | 8/2011 | Ayette et al. | 5/621 |
| 8,001,635 | B2 * | 8/2011 | Humbles | 5/623 |
| 8,146,599 | B2 * | 4/2012 | Wilson et al. | 128/845 |
| 8,214,951 | B1 * | 7/2012 | Batta | 5/647 |
| 8,286,284 | B2 * | 10/2012 | Fee et al. | 5/628 |
| 8,286,285 | B2 * | 10/2012 | Mahler | 5/646 |
| 8,381,734 | B2 * | 2/2013 | Hedges et al. | 128/845 |
| 2003/0192122 | A1 * | 10/2003 | Ames | 5/646 |
| 2004/0221392 | A1 * | 11/2004 | Tsai | 5/626 |
| 2005/0091749 | A1 * | 5/2005 | Humbles | 5/646 |
| 2006/0213011 | A1 * | 9/2006 | McLoughlin et al. | 5/628 |
| 2009/0090370 | A1 * | 4/2009 | Bernstein | 128/845 |
| 2009/0265853 | A1 * | 10/2009 | Maxwell | 5/601 |
| 2010/0005593 | A1 * | 1/2010 | Bowling et al. | 5/627 |
| 2010/0275377 | A1 * | 11/2010 | West | 5/621 |
| 2011/0047706 | A1 * | 3/2011 | Hiebert | 5/623 |
| 2011/0126355 | A1 * | 6/2011 | Hiebert | 5/622 |
| 2011/0219546 | A1 * | 9/2011 | West | 5/621 |
| 2012/0255124 | A1 * | 10/2012 | West | 5/623 |
| 2012/0272451 | A1 * | 11/2012 | Haskell et al. | 5/628 |

\* cited by examiner

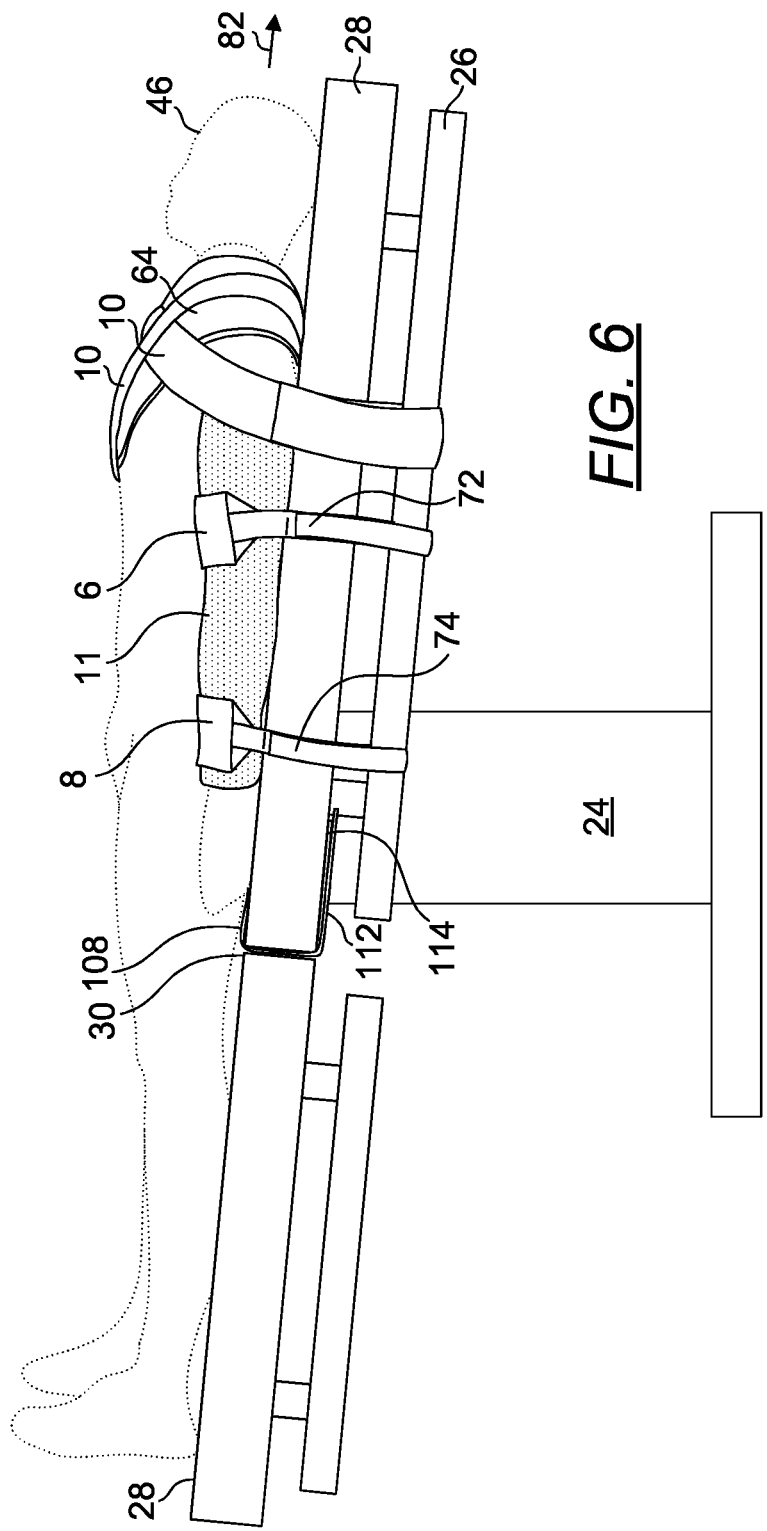

OPERATING TABLE PATIENT POSITIONER AND METHOD

PRIORITY CLAIM AND RELATED APPLICATIONS

This continuation-in-part application claims the benefit of priority from provisional application U.S. Ser. No. 61/215,169 filed May 4, 2009 and non-provisional application U.S. Ser. No. 12/722,610 filed Mar. 12, 2010. Each of these applications is incorporated by reference in its entirety.

BACKGROUND OF THE INVENTION

1. The Field of the Invention

The present invention is directed generally to surgical aid devices, and more particularly, to a patient positioner for maintaining a patient's position while placed atop an operating table in the Trendelenburg, supine, left or right tilt and lithotomy positions.

2. Background Art

Briefly, there are many devices and methods known in the art for maintaining a patient's position on an operating table during an operation. After the patient is positioned on an operating table, the tilt angle and height of the operating table is generally adjusted to facilitate the operating crew's access to a surgical site or to gravitationally move organs out of the way such as in the case of a laparoscopy procedure. When the operating table is tilted in the lengthwise or widthwise direction, the operating crew runs the risk of causing the patient to slide longitudinally, roll laterally or otherwise undesirably change his/her position. A corrective action is then required to move the patient to a position or orientation favorable for access. Such action can be tedious, time-consuming and especially hazardous if the surgical operation is well in progress.

It is a common practice to position a pair of cushioned pads in abutment with the shoulders to prevent the patient from sliding toward the head end of the operating table when the patient is laid flat on the back with the feet higher than the head (known as the Trendelenburg position). In some cases, additional devices are used in conjunction with the shoulder cushion pads to aid in securing a patient in the Trendelenburg position. Another common practice is to use a second combination of apparatus to maintain a patient in the Trendelenburg position. A generally rectangular draw sheet is first disposed atop an operating table, substantially in alignment with the lengthwise and widthwise direction of the operating table. A patient is then positioned atop the draw sheet and a foam pad is placed under each arm to cradle the arm. The draw sheet is then drawn taut, making sure that there is sufficient sheet area adjacent to the arms such that each lateral side of the sheet can be brought from under a padded arm around and over the padded arm and eventually tucked under the patient's torso. While not secured to the operating table or other structure, the draw sheet used in this manner is believed to provide additional restraining value of the patient to the operating table and protection to the arms. A foam pad is then placed over the patient's chest before two large belts are placed criss-cross over the foam pad, such that their ends are secured to the side rails of the operating table in an attempt to compress the foam pad and secure the patient to the operating table. The drawbacks of these approaches are discussed in Applicant's U.S. Ser. No. 12/722,610 application.

U.S. Ser. No. 12/722,610 application provided an operating table patient positioner for maintaining a patient's position during a medical procedure. The patient positioner includes a generally rectangular body anchoring portion with two chest straps, two table straps, two upper arm straps, and two wrist straps. Hook and loop fasteners removably attach the various straps. This device works well, but it has one drawback that is desirously eliminated. To use the '610 device, surgical room preparation personnel crawl under the operating table to secure them.

In view of the foregoing drawing drawbacks, there exists a need for a safe and effective, easy to secure/install operating table patient positioner capable of maintaining a patient's position with respect to the operating table, which once deployed, allows unobstructed access to the patient's abdominal and lower body while the patient is positioned in the Trendelenburg, supine, left or right tilt or lithotomy positions.

SUMMARY OF THE INVENTION

The support base straps disclosed in the '610 application have been replaced to provide an alternative means of securing the positioner to the operating table to eliminate the necessity for having a surgical room preparation personnel crawl under the operating table to secure them. In accordance with the present invention, there is provided an operating table patient positioner for maintaining a patient's position during a medical procedure such that the entire lower body and abdomen are accessible. A conventional operating table has side rails and a break. The patient positioner includes a generally rectangular body anchoring portion having a longitudinally disposed head and tail ends and two transversely disposed opposing side ends. There is provided a pair of spaced apart chest straps, each strap extending substantially longitudinally from the head end of the body anchoring portion. There is also provided a pair of spaced apart table straps, each strap extending substantially longitudinally from the tail end of the body anchoring portion, a pair of upper arm straps, each strap extending substantially transversely from one side end of the body anchoring portion and disposed substantially on the head end of the body anchoring portion. There is also provided a pair of wrist straps, each strap extending substantially transversely from one side end of the body anchoring portion and disposed substantially on the tail end of the body anchoring portion. A generally rectangular substrate backing having a longitudinally disposed head and tail ends and two transversely disposed opposing side ends is disposed substantially concentrically on and fixedly attached to the body anchoring portion.

A loop portion of a hook and loop fastener is disposed substantially on the free end of each table strap which is configured to be removably attached to a hook portion fixedly disposed on a bottom surface of operating table. Each chest, upper arm or wrist strap comprises a complementary set of hook and loop fastening portions disposed substantially on its free end.

In a preferred embodiment, each upper arm strap or wrist strap further comprises a reduced width free end. The portion of the straps that is not directly used to exert downward pressure or coming contact with the padded arms is reduced in size. Frequently during a surgical procedure, the space available on the side rails is limited as there may be stirrups, anesthesia screen or other attachments competing for space on the side rails. Reduced width straps facilitates anchoring of the same on such side rails.

In use, the present operating table patient positioner is placed atop a section of an operating table, preferably the section where the upper torso of a patient is to be positioned, such that the tail end of its substrate backing is adjacent a break in the operating table. A patient is then positioned over the patient positioner such that the upper arm straps and the wrist straps are substantially lined up with the upper arms and forearms of the patient. A substantially rectangular arm support foam is placed under each of the patient's arms and a chest and shoulder support foam shaped to provide support to the chest and shoulders is placed over the chest and shoulders of the patient. Each side end of the substrate backing is wrapped around and over the exterior surface of the arm support foam. The upper arm and wrist straps and their corresponding reduced width free ends are then disposed over the wrapped arms and secured to the side rails of the operating table, thereby securing the arms while leaving the lower body and abdomen of the patient clear of any obstructions. The upper arm and wrist straps are preferably sufficiently large such that they provide sufficient gripping surfaces on the substrate backing as it is supported by its underlying arm support foam. Each of the chest straps is brought from under the patient over a shoulder and the chest protected by the chest and shoulder support foam and secured to a side rail on the opposing side of the chest strap. When installed, the chest straps form a criss-cross configuration over the chest area, exerting slight compression on the chest and shoulder support foam, thereby securing the patient to the operating table.

In one embodiment, the straps and substrate backing are generally made of launderable garment. In a preferred embodiment, the substrate backing is made of a woven drapery netting fabric. The straps are preferably made of webbing or other non-elastic materials.

In another embodiment of the present invention, there is further provided an integral drape capable of covering the entire operating table surface on which a patient is positioned. In this embodiment, the straps, substrate backing and drape are made of a disposable material.

It is a primary object of the present invention to provide a patient positioner that is effective in maintaining a patient's position while placed atop an operating table in the Trendelenburg, supine, left or right tilt and lithotomy positions.

It is another object of the present invention to provide a patient positioner that is capable of being deployed easily without requiring surgical personnel to get under the operating table.

It is yet another object of the present invention to provide a patient positioner that is low cost, simple to manufacture and fabricable using conventional textile technology.

It is a further object of the present invention to provide a patient positioner that is less obstrusive than conventional cushion pad type applications such that the lower body and abdomen are fully accessible.

It is a further object of the present invention to provide a patient positioner that is safe to use and does not cause nerve damage or other negative effects in the patient.

It is a further object of the present invention to provide a patient positioner that is applicable to patients of varying builds and sizes.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification and claims. Also it is to be understood that the phraseology and terminology employed herein are for the purpose of description and should not be regarded as limiting.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6 is a partially transparent side orthogonal view of one embodiment of the present invention illustrating its use on a patient placed in the Trendelenburg position.

Figure 1:
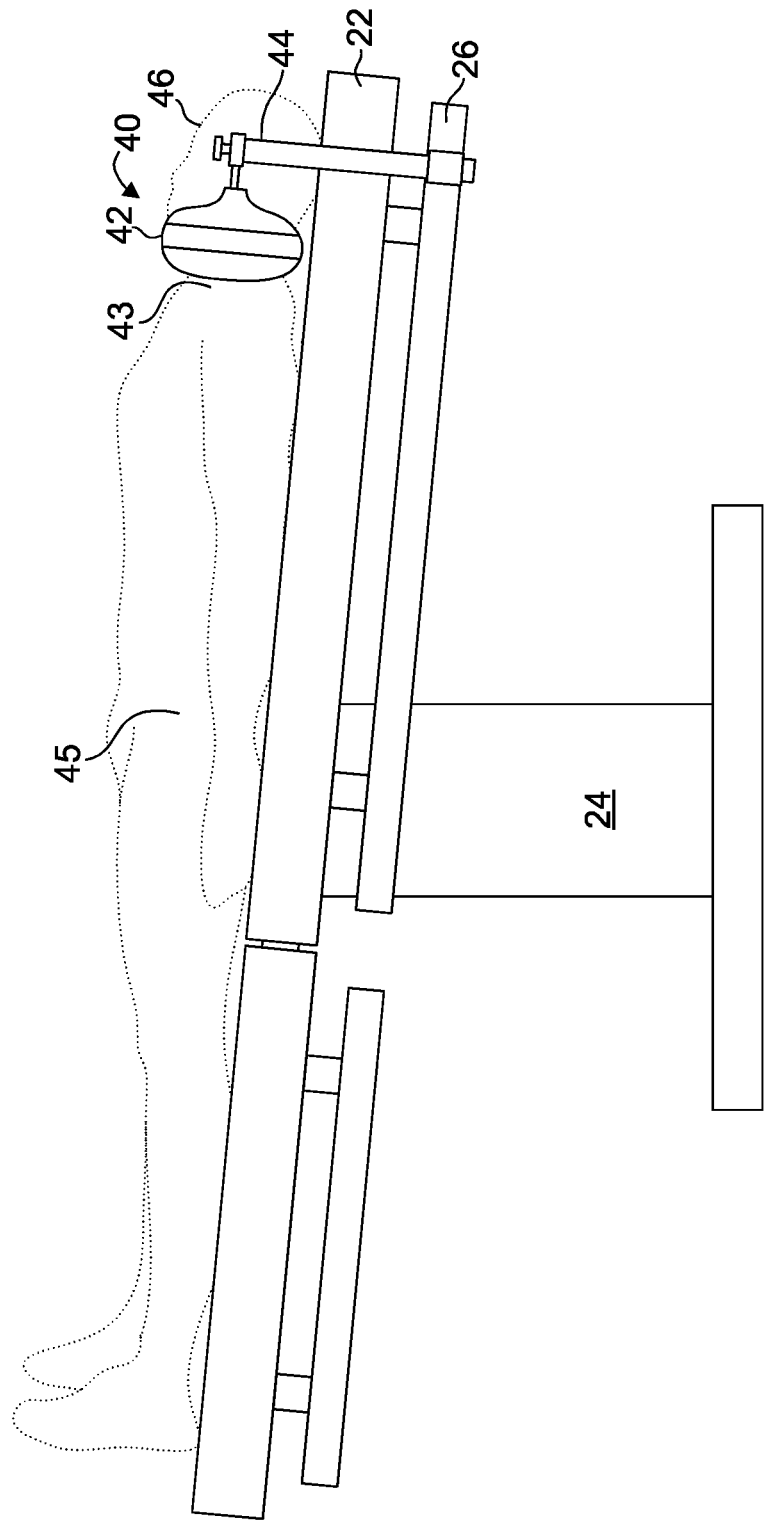
FIG. 1 is a side orthogonal view of a prior art patient positioner being used to support at the shoulder, a patient placed in the Trendelenburg position.

The drawings are not to scale, in fact, some aspects have been emphasized for a better illustration and understanding of the written description.

PARTS LIST

2—operating table patient positioner
4—body anchor portion
5—head end of body anchor portion
6—upper arm strap
7—tail end of body anchor portion
8—wrist strap
9—side (transverse) end of body anchor portion
10—chest strap
11—substrate backing
13—attachment line
14—upper arm strap securing means
15—tail end relief
16—wrist strap securing means
17—head end relief
18—chest strap securing means
19—side (transverse) end of substrate backing 22—operating table
24—support base
26—side rail
28—operating table section
30—break between operating table sections
32—disposable positioner
33—another embodiment of disposable positioner
34—cuts for straps
38—drape
39—drape with cuts for straps
40—prior art patient positioner
42—cushioned pad
43—shoulder of patient
44—support structure
45—waist of patient
46—patient
47—upper arm of patient
48—length of chest strap
50—length of upper arm strap
51—length of wrist strap
52—length of reduced upper arm strap
53—length of reduced wrist strap
54—distance between upper arm strap and wrist strap
55—distance between chest straps
56—distance between table straps
57—width of chest strap
58—width of table strap
59—width of upper arm strap
60—width of wrist strap
62—arm support foam
64—chest and shoulder support foam
66—arm
68—longitudinal dimension of substrate backing
70—transverse dimension of substrate backing
72—reduced upper arm strap
74—reduced wrist strap
76—chest of patient
78—shoulder of patient
80—forearm of patient
82—tendency of patient to slide off operating table
84—foam pad
86—belt
88—draw sheet
90—edge where draw sheet is tucked under the patient
92—prior art patient positioner
94—drape length
96—drape width
98—attachment line to secure substrate backing to a chest or table strap
108—table strap
110—length of table strap
112—table strap securing means
114—table strap receiving means
116—length of table strap securing means

DEFINITIONS OF TERMS USED IN THIS SPECIFICATION

The aforementioned flexible structure having a body anchoring portion, a substrate backing and a plurality of straps attached to the body anchoring portion adapted for maintaining a patient's position on an operating table shall have equivalent nomenclature including: the patient positioner, positioner, the operating table patient positioner, the present invention, or the invention. Also, the term rectangular is understood to include the case where all sides of the geometric shape are of equal length, also known as an equilateral rectangle or a square.

PARTICULAR ADVANTAGES OF THE INVENTION

The present invention provides an operating table patient positioner that effectively secures a patient to an operating table in the Trendelenburg, left and right tilt, supine and lithotomy positions without causing bruising or nerve damage. Several features and advantages of the present positioner have previously been disclosed in co-pending application U.S. Ser. No. 12/722,610. In the embodiment disclosed herein, there is an improvement. The support base straps disclosed in the '610 application have been replaced to provide an alternative means of securing the positioner to the operating table to eliminate the necessity for having a surgical room preparation personnel crawl under the operating table to secure them. A hook and loop fastener securely attaches the positioner to the operating table.

DETAILED DESCRIPTION OF A PREFERRED EMBODIMENT

Various devices have been adapted to support a patient 46 positioned on an operating table 22. FIG. 1 is a side orthogonal view of a prior art device being used to support a patient 46 placed in the Trendelenburg position (feet elevated higher than the head). Support is provided at the patient's shoulders. Patient slipping occurs while the operating table 22 is adjusted in various angles, however, problems associated with patient movement are most pronounced in the Trendelenburg position. In the patient position depicted in FIG. 1, if unrestricted by the prior art device 40, the patient will most likely start sliding down toward the head even when positioned with the slightest grade. The prior art device 40 has a pair of cushioned pads 42, each supported on a support structure 44 which is in turn fixedly attached to a sturdy structure such as a side rail 26 of the operating table 22. In use, the cushioned pads are brought into abutment with the patient's 46 shoulders to prevent the patient from sliding down. If left or right tilt is expected or if additional restraint is desired, a cushioned pad can additionally be positioned against each side of the patient's waist 45 to restrict the patient's lengthwise and lateral slide or lateral roll movements.

If the patient is positioned such that he/she is expected to inadvertently slide down toward the feet (in the reverse Trendelenburg position), a common practice is to position a restraint in the form of a flat foot plate at the feet of the patient to curb such a movement.

Thus, prior art common practice uses one set of individual and dedicated positioners to restrict patient movement in one particular direction. In accordance with the prior art, if the patient is to be positioned such that sliding is restricted in the Trendelenburg, reverse Trendelenburg, or left and right tilt positions, all three sets of aforementioned devices would be required. If access is required in the lower body or abdomen, the positioner disposed at the waist or the positioner disposed at the feet may pose a challenge to overcome and be a physical obstruction. During a given medical procedure, a patient is routinely moved through the various aforementioned positions. The step of dismantling a patient positioner to allow access during a medical procedure is time-consuming, distracting and highly undesirable.

A more serious problem is associated with the use of prior art cushioned pads on the shoulders. A prolonged exposure to the cushioned pads in the Trendelenburg position can cause bruising and/or nerve lesion to develop in the patient's shoulders due to elevated pressure from the patient's own weight as it is exerted at the shoulders. A similar hazard can develop in the waist if the patient is tilted to one side at an angle sufficiently severe to develop high pressure in the waist. There exists a need for a positioner that is capable of maintaining a patient in the Trendelenburg, left and right tilt, supine and lithotomy positions while allowing access to the lower body and abdomen and without causing such nerve injury in the patient.

Figure 1A:
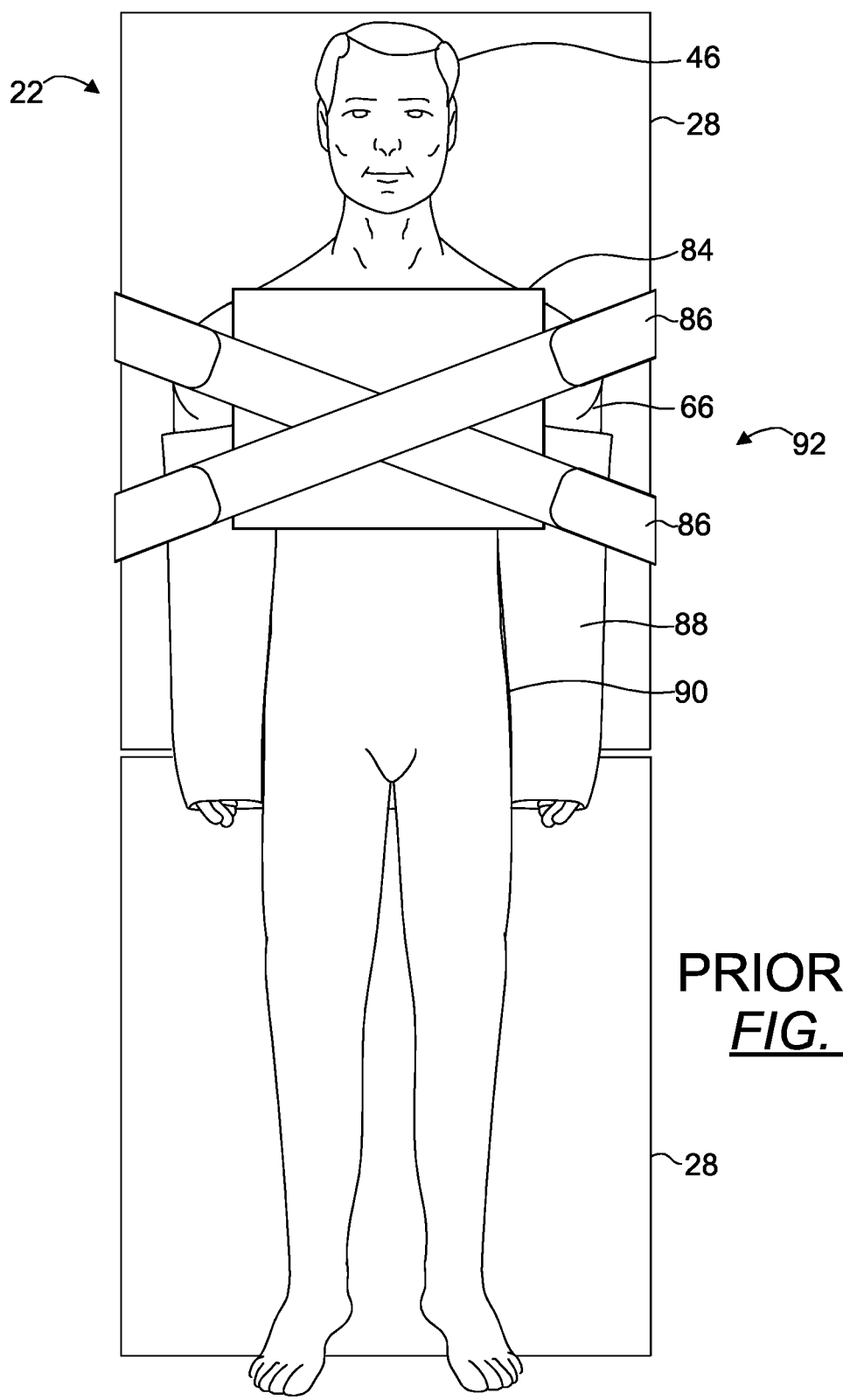
FIG. 1A is a front orthogonal view of a prior art patient positioner being used to support at the chest and arms, a patient placed in the Trendelenburg position.

FIG. 1A is a top orthogonal view of another prior art device 92 being used to support a patient placed in the Trendelenburg position. This device provides support at the chest and arms. A draw sheet 88 is placed under the patient's torso and a foam pad is placed under each of the patient's arms 66. The transverse side edges of the draw sheet 88 are then brought around and over the foam pad-protected arms and tucked under the patient's torso at the edge indicated as 90 on FIG. 1A. A foam pad 84 sized to cover substantially the chest area is then positioned over the patient's chest in the criss-cross fashion. Two large belts 86 are then provided to secure the foam pad down on the patient's chest. Each of the belts has two ends, wherein an attaching means is disposed on each end. In this example, each end of each of the belts is secured to the side rails (not visible) located at the bottom periphery of the operating table 22. This device does not conform well to the patient's body (especially chest and shoulders) contour and is simply positioned across the chest. As such, this device lacks the ability to prevent the patient from sliding when positioned in the Trendelenburg position.

Figure 2:
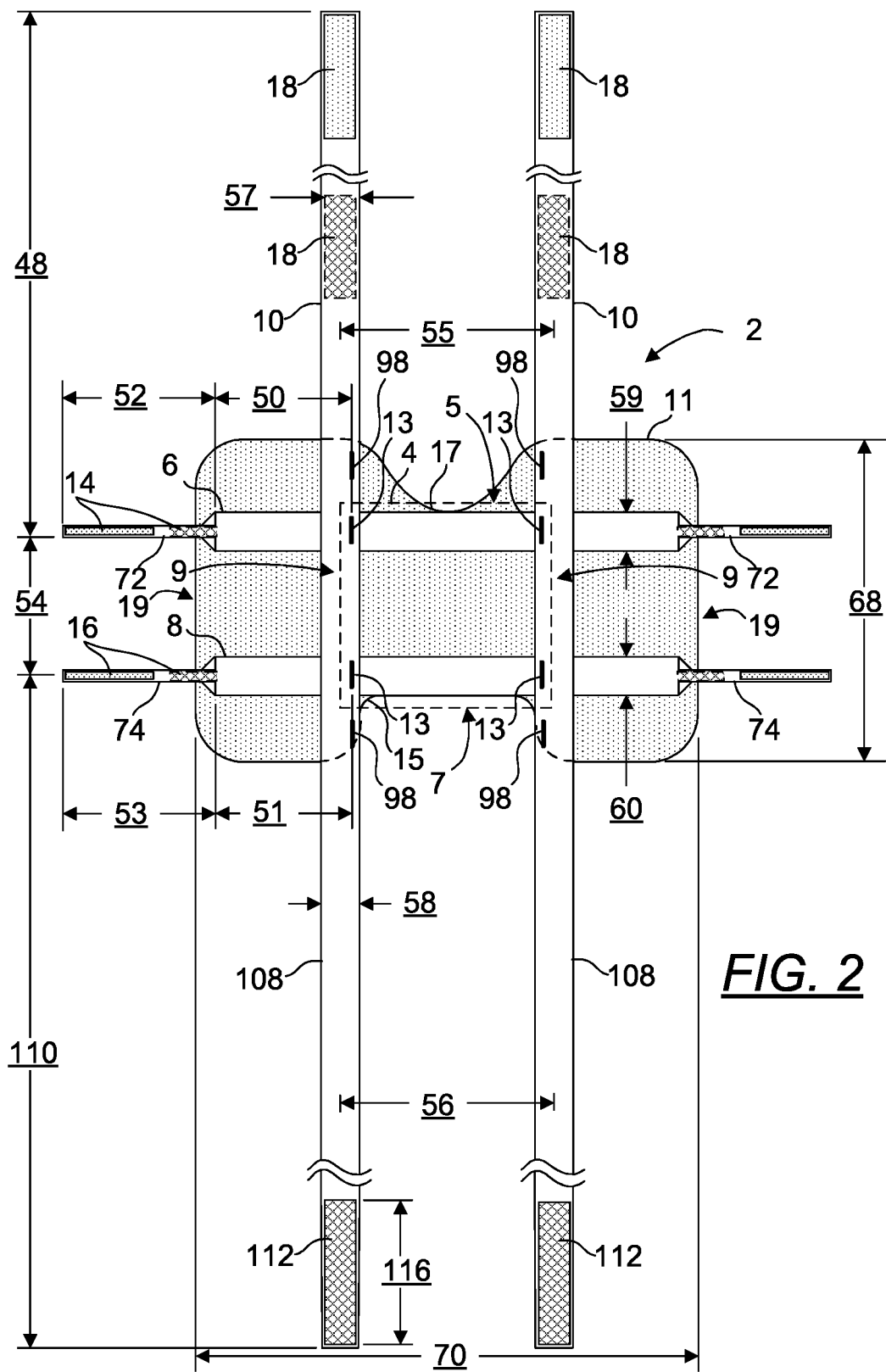
FIG. 2 is a front orthogonal view of one embodiment of the present invention.

FIG. 2 is a front orthogonal view of one embodiment of the present invention illustrating an operating table patient positioner 2 in its unfurled and spread out configuration. The positioner 2 comprises a generally rectangular body anchoring portion 4 having longitudinally disposed head 5 and tail 7 ends and two transversely disposed side ends 9. The positioner 2 is placeable atop an operating table during use. In the ensuing description, the orientation of the positioner 2 and other parts of the positioner 2 will be referenced to the orientation of the body anchoring portion 4.

Four pairs of straps cooperate to secure the patient on the operating table: chest straps 10, table straps 108, upper arm straps 6 and wrist straps 8. The pair of chest straps 10 is spaced apart, extending outwardly from the head end of the body anchoring portion 4 and disposed substantially longitudinally of the patient positioner 2. The pair of spaced apart table straps 108 extends outwardly from the tail end of the body anchoring portion 4 and is also disposed substantially longitudinally of the patient positioner 2. Each of the upper arm straps 6 extends outwardly from one side end 9 of the body anchoring portion 4 and is disposed substantially transversely of the patient positioner 2 and substantially adjacent the chest straps 10. Each of the wrist straps 8 extends outwardly from each side end 9 of the body anchoring portion 4 and is disposed substantially transversely of the patient positioner 2 and substantially adjacent the table straps 108.

There is further provided a substrate backing 11 that is fixedly attached to the body anchoring portion 4 substantially at its outer periphery at attachment lines 13. The substrate backing 11 is a generally rectangular fabric disposed concentrically with the body anchoring portion 4. First and second longitudinally disposed semi-circular cutouts 17, 15 are made in the head 5 and the tail 7 ends of the substrate backing 11, respectively, to facilitate positioning and adjustment of the two transversely disposed side ends 19 of the substrate backing 11 over the arms of a user while in use and allow the use of the positioner on varying sized patients. In addition, the second cutout 15 functions to reduce possible contact with surgical contamination at the lower body or abdomen which is particularly important for a reusable patient positioner. The cutouts 15, 17 also reduce material costs. As will be readily appreciated, cutouts 15, 17 may be formed in various shapes and dimensions.

The dimensions of the substrate backing 11 are configured such that the longitudinal 68 and transverse 70 dimensions are sufficient to provide coverage and support to the upper arm 6 and wrist straps 8. In a preferred embodiment, each chest strap 10 is connected to a table strap 108 and is integrally constructed as a single strap. In a similar manner, the two upper arm straps 6 are integrally joined together and constructed as a single strap. In a similar manner, the two wrist straps 8 are also joined together and constructed of a single strap. In a preferred embodiment, the chest 10, table 108, upper arm 6 and wrist straps 8 are fixedly attached (for example via stitching or adhesive) at attachment lines 13 where the straps cross one another. The attachment lines 13 are preferably disposed on the inner edges of the chest/table straps 10, 108 to allow more flexibility in the range of motion on the upper arm and wrist straps 6, 8. The substrate backing 11 is secured to the body anchoring portion 4 at attachment lines 13 and attachment lines 98 disposed substantially at the longitudinal periphery of the substrate backing 11 and on the inner edges of the chest/table straps 10, 108.

In one embodiment, the straps 6, 8, 10, 108 and substrate backing 11 are constructed from a launderable material capable of being reused repeatedly. In other aspects, the positioner 2 is disposable.

In the preferred embodiment as depicted, the upper arm 6 and the wrist 8 straps are terminated with strap portions of reduced width 72, 74 at the free ends. As will be appreciated, the upper arm 6 and wrist straps 8 do not have to be terminated with reduced widths. In one embodiment not shown, the upper arm 6 and wrist 8 straps are constructed of straps of constant width throughout their length. There is further provided a complementary hook and loop attaching means on the free end of each of the chest 10, reduced width upper arm strap portion 72 and reduced width wrist strap portion 74 such that a loop can be formed at each of the free ends for securing the patient positioner 2 to an operating table. The length 48 of the chest straps preferably ranges from 65 to 70 inches while the width 57 preferably ranges from 3 to 5 inches.

The length 110 of the table straps preferably ranges from 10 to 40 inches while the width 58 preferably ranges from 3 to 5 inches. The table straps 108 are preferably spaced apart a distance 56 ranging from 7 to 10 inches. A table strap securing means 112 is preferably disposed on a free end of each table strap 108.

The dimensions 50, 52, 59 of the upper arm straps and the reduced width upper arm strap portions are preferably substantially similar to the dimensions 51, 53, 60 of the wrist straps and the reduced width wrist strap portions, respectively. The length 50 of the upper arm straps preferably ranges from 12 to 19 inches while the width 59 preferably ranges from 2 to 4 inches. The length of the strap portions with reduced width 52 preferably ranges from 14 to 18 inches. The chest straps are preferably spaced apart a distance 55 ranging from 7 to 10 inches. The table straps are preferably spaced apart a distance 56 ranging from 7 to 10 inches. The upper arm and wrist straps are preferably spaced apart a distance 54 ranging from 6 to 8 inches. The longitudinal dimension 68 of the support backing preferably ranges from 24 to 36 inches while the transverse dimension 70 of the support backing preferably ranges from 27 to 40 inches.

Figure 3:
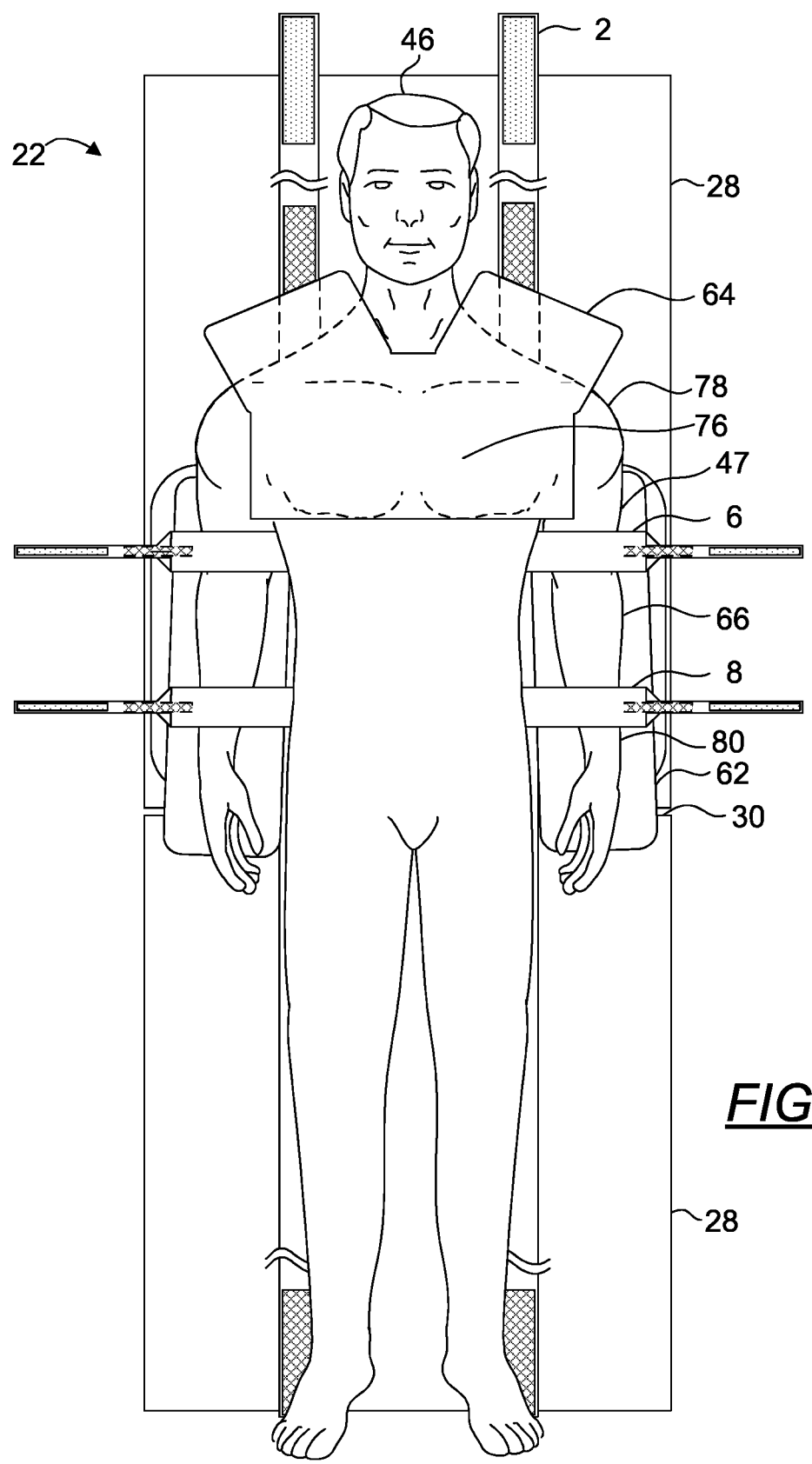
FIG. 3 is a partially transparent front orthogonal view of one embodiment of the present invention illustrating the relative position of a patient positioner of FIG. 2 with respect to the placement of a patient and additional positioner aid.

FIG. 3 is a partially transparent front orthogonal view of one embodiment of the present invention illustrating the relative position of a positioner 2 of FIG. 2 with respect to the placement of a patient and additional positioner aids such as arm supports and chest and shoulders foam pads. In use, a positioner 2 is placed on an operating table 22 having two sections 28 with the longitudinal axis defined as substantially parallel to the operating table's lengthwise direction. A patient 46 is then positioned on top of the patient positioner 2 such that the torso is placed over the body anchoring portion 4, effectively anchoring the positioner 2 to the operating table 22. The patient 46 is also positioned such that the patient's upper arms 47 are substantially lined up with the upper arm straps 6 and the patient's forearms 80 are substantially lined up with the wrist straps 8. A substantially rectangular arm support foam 62 is placed under each patient's arm 66 and a chest and shoulder support foam 64 shaped to provide support to the chest and shoulders is placed over the chest 76 and shoulders 78 of the patient 46. In use, the body anchoring portion 4 of the patient positioner 2 is preferably placed entirely on one section 28 of the operating table 22 leaving the break 30 between the two sections 28 close to but not covered by the tail end 7 of the body anchoring portion 4.

Figure 4:
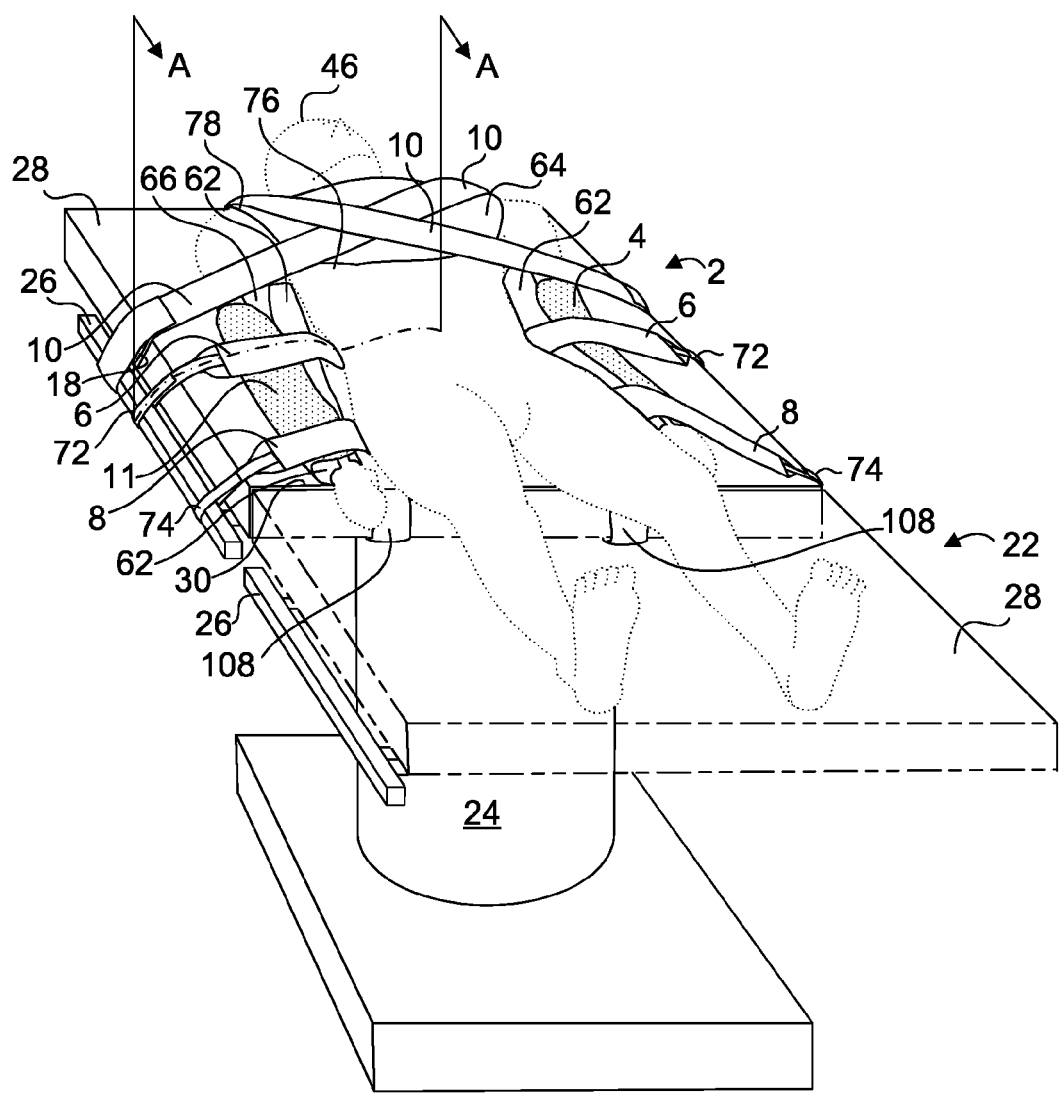
FIG. 4 is a partially transparent front perspective view of one embodiment of the present invention illustrating its use on a patient placed in the Trendelenburg position.

FIG. 4 is a partially transparent front perspective view of one embodiment of the present invention illustrating its use on a patient placed in the Trendelenburg position. The operating table 22 is made up of two sections 28 forming a break 30 therebetween and a side rail 26 disposed substantially at the longitudinal bottom periphery of each section. One or both sections 28 are directly supported on a support base 24. It is to be understood that the positioner 2 is capable of being used on other types of operating tables, provided that the straps 10, 108, 6, 8, 72, 74 are sufficiently long and able to form securing loops around the equivalent support structure.

Figure 5:
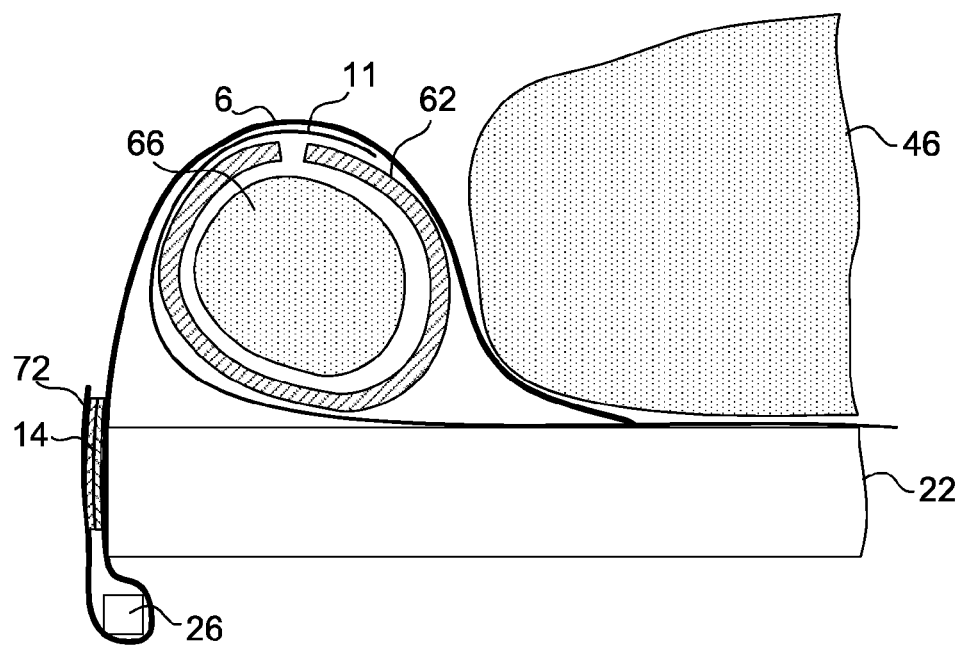
FIG. 5 is an orthogonal sectional view taken along line AA of FIG. 4 illustrating the relative position of an upper arm strap with respect to the placement of a substrate backing and arm support foam while in use.

Prior to deploying a patient positioner 2, the operating table 22 is brought to a level configuration to prevent gravitational tendency from causing the patient positioner 2 or patient 46 to roll off the operating table 22. First, a patient positioner 2 is placed atop a section 28, preferably the section 28 where the upper torso of a patient 46 is to be positioned such that the tail end of its body anchoring portion 4 comes close to but not over the break 30. The positioner 2 is then secured to the operating table by attaching a pair of table straps 108 to the bottom surface of the operating table. A patient 46 is then positioned over the positioner 2 such that the upper arm straps 6 and the wrist straps 8 are substantially lined up with the upper arms and forearms of the patient 46. A substantially rectangular arm support foam 62 is placed under each of the patient's arms 66. A chest and shoulder support foam 64 shaped to provide support to the chest and shoulders is placed over the chest 76 and shoulders 78 of the patient 46. In FIG. 5, a cutaway view is provided to illustrate how an upper arm strap 6 is used in conjunction with the substrate backing 11 and arm support foam 62 to secure a part of a patient to an operating table 22.

FIG. 5 is an orthogonal sectional view taken along line AA of FIG. 4 illustrating the relative position of an upper arm strap 6 with respect to the placement of the substrate backing 11 and arm support foam 62 while in use. As depicted, a portion of a patient 46 is positioned on top of a portion of the positioner, i.e., an upper arm strap 6 and part of the substrate backing 11. An arm support foam 62 is wrapped around the arm 66 at the upper arm, substantially covering the entire circumference of the arm 66 in order to cradle the arm 66. One side end of the substrate backing 11 is then wrapped around and over the exterior surface of the arm support foam 62. A reduced width upper arm strap portion 72 is pulled through the gap between the patient 22 and his/her arm 66 and wrapped over the arm 66 and eventually pulled through a gap made between the operating table 22 and the side rail 26 to form a loop around the side rail 26 and secured using attaching means 14. As depicted, hook and loop fastening portions are used.

Referring to FIGS. 4 and 5, each side end of the substrate backing 11 is shown wrapped around and over the outside of the arm support foam 62 and the upper arm and wrist straps 6, 8 and their corresponding reduced width end portions 72, 74 are disposed over the arms and secured to the side rails of a section 28, thereby securing the arms while leaving the lower body of the patient clear of any obstructions. The upper arm and wrist straps 6, 8 are preferably configured sufficiently large such that they provide sufficient grip on the substrate backing 11 as it is supported by its underlying arm support foam 62. Each of the chest straps 10 is brought from under the patient 46 over a shoulder 78 and the chest 76 protected by the chest and shoulder support foam 64 and secured to a side rail 26 on the opposing side of the chest strap 10. When installed, the chest straps form a criss-cross across the chest area, exerting slight compression on the chest and shoulder support foam 64, thereby securing the patient 46 to the operating table 22. Unlike the cushioned pads 42 used in the prior art positioner 40, the novel straps 10, 6, 8 provided by the present invention enable the patient to be secured using friction effected over a wider area across the chest and arm surfaces, thereby eliminating pressure points experienced with prior art cushioned pads. The chest, reduced width upper arm and wrist strap portions 10, 72, 74 comprise securing means 18, 14, 16 at their free ends respectively. In a preferred embodiment, each of the securing means 18, 14, 16 comprises hook and loop fastening portions. Alternatively, each strap may be secured to the side rail 26 by tying its free end to the side rail 26. In contrast to the prior art positioner disclosed in FIG. 1A, the present invention provides enhanced grip by having a significantly larger contact area between the patient and the positioner due to the increased surface areas afforded by the table straps, upper arm, wrist and chest straps, securement of the upper arm, wrist and chest straps to the operating table at the side rails and a positive securement at the table straps. In addition, the present invention includes a pair of chest straps that are brought around and over the shoulders which further provides securement of the patient.

Figure 6A:
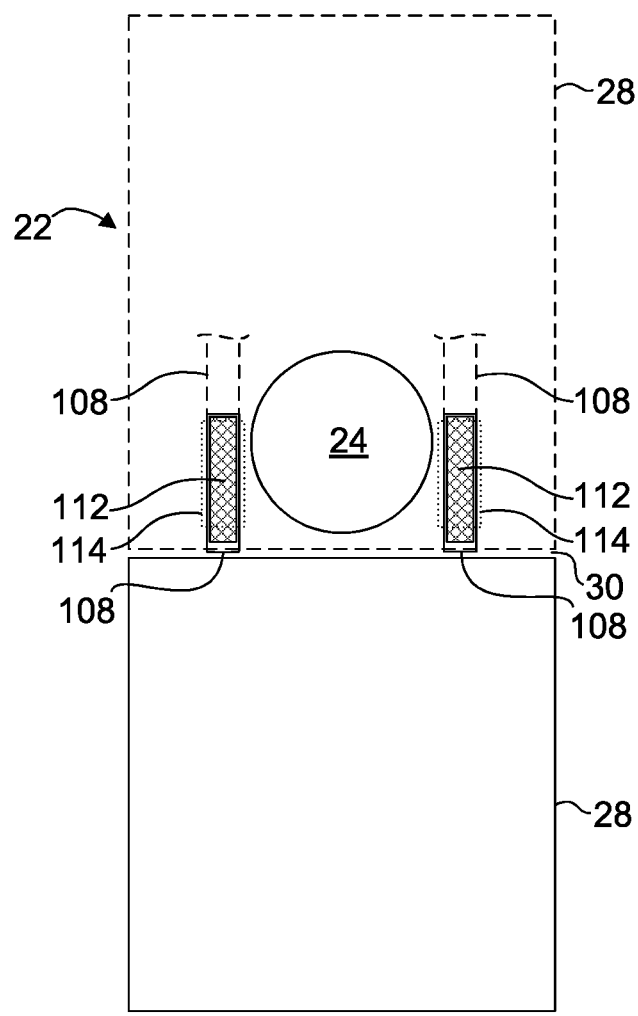
FIG. 6A is a partially transparent front orthogonal view of the present positioner in use with the patient and other parts of the positioner removed for clarity.

FIG. 6 is a partially transparent side orthogonal view of one embodiment of the present invention illustrating its use on a patient placed in the Trendelenburg position. FIG. 6A is a partially transparent bottom orthogonal view of the present positioner in use with the patient and other parts of the positioner removed for clarity. Referring to FIGS. 4, 6 and 6A, each of the table straps 108 is slid through a break 30 in an operating table 22 and secured to a portion of the bottom surface of the operating table 22 in a manner such that the tendency for the patient 46 to slide down head first is partially prevented by tension exerted in the table straps 108. There is provided a pair of table strap receiving means 114 disposed on a portion of the bottom surface of the operating table 22. In a preferred embodiment, the table straps 108 are secured by means of matingly disposing a table strap securing means 112 over a table strap receiving means 114. In a preferred embodiment, each table strap securing means 112 is a loop portion of a hook and loop fastener although a hook portion will also work. Each table strap receiving means 114 is preferably a hook portion of a hook and loop fastener. Since the table strap receiving means 114 does not come in direct contact with a patient or other contaminants such as surgical wastes, it can be reused indefinitely. A hook portion is generally more durable than a loop portion in a hook and loop fastener, thereby making the hook portion a preferred choice for use as the table strap receiving means 114. The length 116 of the loop portion preferably ranges from about 20 to about 50 inches. When used on an operating table without a break 30 between sections 28, the table straps 108 may alternatively be secured by tying each strap 108 to a side rail 26. The use of the table straps 108 and their associated attaching means as disclosed in FIGS. 4 and 6 provides a convenient way for securing the positioner at one end to the operating table 22.

In view of the foregoing descriptions, it is apparent that the patient's tendency to slide off of the head end of the operating table as indicated by arrow 82 is curtailed by providing the present novel patient positioner having greater patient engaging surfaces. The present novel patient positioner provides benefits in many areas. By having all of the straps fixedly attached as a single unit, all patient contacting surfaces are connected together and cooperate to provide sufficient friction to retain the patient in the Trendelenburg position. Since the effective contact area between the patient 46 and the positioner 2 is large, the potential to develop pressure points in the patient 46 is greatly reduced or eliminated. An added benefit of having multiple straps connected as a single unit is in the fail safe aspect of the patient positioner 2. In circumstances where one or more straps become detached during use, there are remaining straps which are still secured to the operating table. In addition, having multiple straps connected as a single unit also serves as a reminder to surgical personnel to properly secure a patient. In contrast to the practice of using only two straps secured over the chest area of a patient, the present patient positioner provides a positive securement of the positioner and the patient by securing the positioner 2 to the operating table 22 in a direction opposing the tendency to slide.

Figure 7:
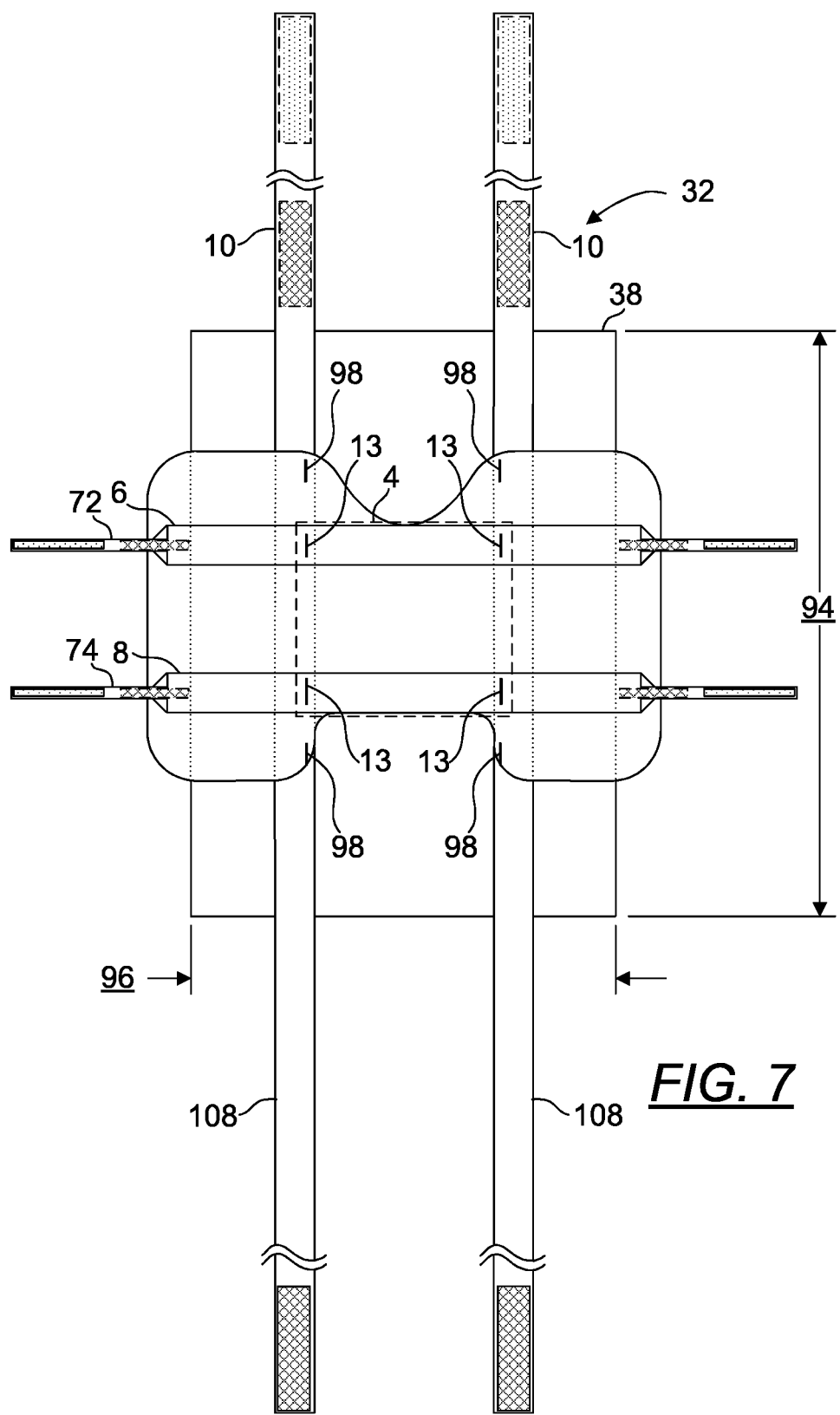
FIG. 7 is a partially transparent front orthogonal view of one embodiment of the present invention.

FIG. 7 is a partially transparent front orthogonal view of an alternate embodiment of the present invention. In this embodiment, the positioner 32 is made from a disposable material comprising an additional drape 38, wherein the drape 38 is a generally rectangular sheet disposed substantially concentrically with the body anchoring portion 4. The relative positioning and sizes of all of the straps 10, 108, 6, 8, 72, 74, substrate backing 11 and the body anchoring portion 4 and attachment lines 13, 98 are substantially similar to the positioner 2 disclosed in FIG. 2. The positioner 32 is constructed by first laying down a drape 38, followed by a pair of unitary chest/table straps 10, 108, a substrate backing 11 and lastly a pair of unitary upper arm 6 and wrist straps 8 and their corresponding reduced width free ends 72, 74. All layers are then fixedly attached at attachment lines 13, 98 such that the flexibility of all of the straps 10, 108, 6, 8, 72, 74 and the side ends 19 of the substrate backing 11 is unimpeded. The length 94 of the drape 38 preferably ranges from 55 to 65 inches while the width 96 of the drape 38 preferably ranges from 35 to 45 inches. In use, the drape 38 provides protection to an operating table on which a patient is positioned negating the necessity of providing a separate drape underneath a positioner 32, thereby simplifying room preparation.

Figure 8:
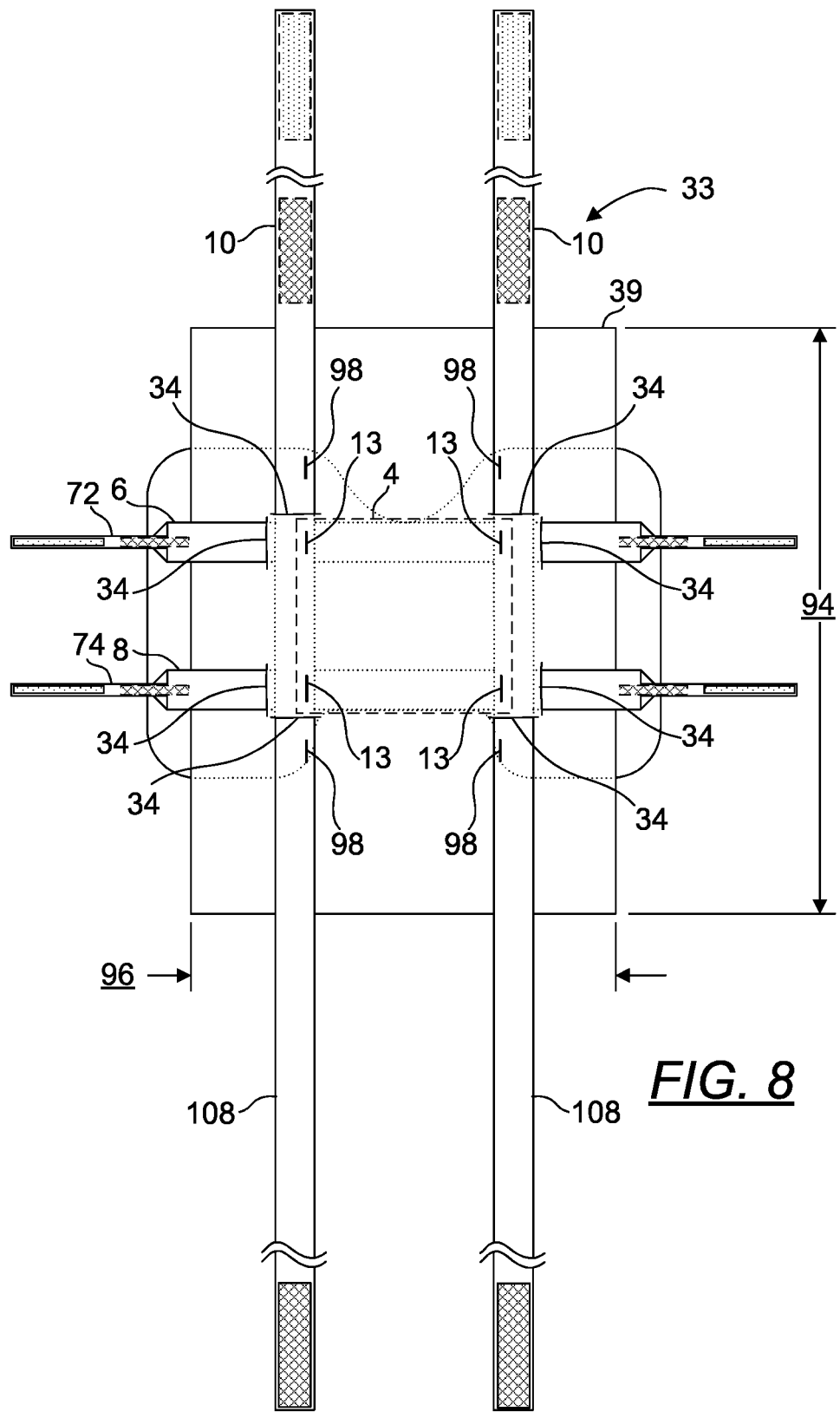
FIG. 8 is a partially transparent front orthogonal view of one embodiment of the present invention.

FIG. 8 is a partially transparent front orthogonal view of an alternate embodiment of the patient positoner 32 disclosed in FIG. 7. In this embodiment, the positioner 33 is made from a disposable material comprising also an additional drape 39, wherein the drape 39 is a generally rectangular sheet having a cut 34 made for each strap 10, 108, 6, 8 and each cut 34 is positioned substantially at right angle to and at the root of each strap where each strap is attached to the body anchoring portion 4. Each strap 10, 108, 6, 8 is routed through the opening created by each of the cuts 34 and pulled taut before it is secured to the drape 39 at attachment lines 98 and 13 such that the positioner 33 is disposed substantially concentrically with the body anchoring portion 4 and further strengthened. The length 94 of the drape 39 preferably ranges from 55 to 65 inches while the width 96 of the drape 39 preferably ranges from 35 to 45 inches. In use, the drape 39 provides protection to an operating table on which a patient is positioned negating the necessity of providing a separate drape underneath a positioner 33, thereby simplifying room preparation.

It will be appreciated by those skilled in the art that while the invention has been described above in connection with particular embodiments the invention is not necessarily so limited and that numerous other embodiments, uses, modifications and departures from the embodiments, and uses may be made without departing from the inventive concepts.

The invention claimed is:

1. A patient positioner for maintaining a patient's position during a medical procedure that occurs while the patient is supported on an operating table, whereby the entire lower body and abdomen of the patient are accessible, said patient positioner comprising:

a generally rectangular body anchoring portion having longitudinally disposed head and tail ends and two transversely disposed opposing side ends, placeable atop the operating table, said longitudinally disposed head and tail ends of said generally rectangular body anchoring portion defining a lengthwise direction;

a pair of spaced apart chest straps, each chest strap extending substantially in said lengthwise direction from said head end of said body anchoring portion to a free end and having a chest strap attaching means disposed on said free end of said each chest strap;

a pair of spaced apart table straps, each table strap extending substantially in said lengthwise direction from said tail end of said body anchoring portion to a free end and having a table strap securing means disposed on said free end of said each table strap and configured to cooperate with a receiving means configured to be disposed on a portion of the operating table and to secure each said table strap at each said table strap securing means;

a pair of upper arm straps, each said upper arm strap extending substantially transversely from one of said two transversely disposed opposing side ends of said body anchoring portion to a free end and disposed substantially adjacent said head end of said body anchoring portion and having an upper arm strap attaching means disposed on said free end of said each upper arm strap;

a pair of wrist straps, each said wrist strap extending substantially transversely from one of said two transversely disposed opposing side ends of said body anchoring portion to a free end and disposed substantially adjacent said tail end of said body anchoring portion and having a wrist strap attaching means disposed on said free end of said each wrist strap; and a generally rectangular substrate backing having longitudinally disposed head and tail ends and two transversely disposed opposing side ends, said generally rectangular substrate backing is substantially concentrically disposed on said body anchoring portion and at least a portion of said generally rectangular substrate backing is fixedly attached to said body anchoring portion, wherein at least one of said chest strap attaching means, said upper arm strap attaching means and said wrist strap attaching means comprises complementary hook and loop fastening portions and wherein said generally rectangular substrate backing is disposed below said pair of upper arm straps and said pair of wrist straps.

2. The patient positioner of claim 1, wherein each said chest strap is connected to one of said table straps and formed as a single continuous unit and fixedly secured to said body anchoring portion.

3. The patient positioner of claim 1, wherein said pair of upper arm straps is joined together and formed as a single continuous unit and fixedly secured to said body anchoring portion.

4. The patient positioner of claim 1, wherein said pair of wrist straps is joined together and formed as a single continuous unit and fixedly secured to said body anchoring portion.

5. The patient positioner of claim 1, wherein said side ends of said substrate backing are made substantially broad such that they are capable of being wrapped around and over the patient's arms while said substrate backing is placed underneath the patient's back on the operating table.

6. The patient positioner of claim 5, wherein said substrate backing further comprises a first cutout disposed centrally on said head end of said substrate backing and a second cutout disposed centrally on said tail end of said substrate backing.

7. The patient positioner of claim 1, wherein said patient positioner is made of a fabric material capable of being laundered and reused repeatedly.

8. The patient positioner of claim 1, wherein said patient positioner is disposable.

9. The patient positioner of claim 8, wherein said patient positioner further comprises a substantially rectangular drape disposed substantially concentrically to said body anchoring portion, wherein said patient positioner is constructed by laying down materials in an order of said drape, said chest and table straps, said substrate backing and said upper arm and wrist straps and fixedly securing all said materials in said order such that flexibility of all said straps and said side ends of said substrate backing is unimpeded.

* * * * *